United States Patent [19]

Lang et al.

[11] Patent Number: 5,197,835
[45] Date of Patent: Mar. 30, 1993

[54] WORK-BENCH WITH A SAFETY DEVICE

[75] Inventors: Hans-Walter Lang; Josef Wenger, both of Leutkirch, Fed. Rep. of Germany

[73] Assignee: Kaltenbach & Voigt GmbH & Co., Biberach an der Riss, Fed. Rep. of Germany

[21] Appl. No.: 728,115

[22] Filed: Jul. 10, 1991

[30] Foreign Application Priority Data

Jul. 10, 1990 [DE] Fed. Rep. of Germany ....... 4021954

[51] Int. Cl.⁵ .............................................. B23C 9/00
[52] U.S. Cl. .................................. 409/134; 144/251 A
[58] Field of Search ........................... 409/134, 229; 144/134 A, 251 A, 251 B, 251 R; 51/268; 83/544

[56] References Cited

U.S. PATENT DOCUMENTS

| 694,835 | 3/1902 | Cook | 144/251 A |
|---|---|---|---|
| 871,533 | 11/1907 | Streich | 144/251 A |
| 1,160,219 | 11/1915 | Wacholz | 144/251 A |
| 1,758,834 | 5/1930 | Heston et al. | 144/134 A |
| 2,895,518 | 7/1959 | Rhett | 144/251 A |
| 3,859,950 | 1/1975 | York | 144/251 A |
| 4,741,370 | 5/1988 | Heaton | 409/229 |

FOREIGN PATENT DOCUMENTS

| 650275 | 9/1928 | France | 144/251 A |
|---|---|---|---|
| 2362709 | 4/1978 | France | 144/134 A |
| 1462177 | 1/1977 | United Kingdom . | |

OTHER PUBLICATIONS

Harnisch+Rieth, *Zahnkranz-Modellschleifer G-F 316*, Apr. 10, 1986, all pages.

*Primary Examiner*—William Briggs
*Attorney, Agent, or Firm*—Scully, Scott, Murphy & Presser

[57] ABSTRACT

Work-bench for machining dental elements, fitted with a safety device. The invention relates to a work-bench for machining dental elements such as denture models or the like comprising a housing, a driving motor located in the housing, a milling cutter that projects above the housing and is driven by the motor, and a bearing member for the dental element to be machined that is arranged above the milling cutter and is movable relative thereto, wherein, to provide a simple form of workpiece bearing member and safety device, together with easy changing of the milling cutter and simple dust removal, said support can pivot about a vertical axis above said milling cutter and can also be swung away from said milling cutter about a horizontal axis.

12 Claims, 2 Drawing Sheets

WORK-BENCH WITH A SAFETY DEVICE

TECHNICAL FIELD OF THE INVENTION

The invention relates to a work-bench for machining dental elements such as denture models or the like comprising a housing, a driving motor located in the housing, a milling cutter that projects above the housing and is driven by the motor, and a bearing member for the dental element to be machined that is arranged above the milling cutter and is movable relative thereto.

BACKGROUND OF THE INVENTION AND PRIOR ART

The publication entitled "Harnisch & Kieth, plaster model location grinder G-F 316" discloses a work-bench of this kind in the form of a grinding machine for cutting locating notches into the bottom of models. The model is moved manually on a Teflon support in a guide against a cemented carbide formed milling cutter, so that the locating notches are milled precisely to shape. The resulting dust is sucked off by built-in exhaust means and deposited in a dust bag. The milling cutter is covered by a movable shield.

In this arrangement the design of the model support, the exhaust means and the safety device is still rather complicated. In particular it is difficult to change the cutter, since the milling table can only be removed with great difficulty and with a special tool. This requires a considerable expenditure of time and effort.

It is also known from British specification 14 62 177, in the case of a high-speed mixer having a shaft that is driven by a hydraulic motor, carries mixing blades and can be raised and lowered so that in the lowered position it extends into a container for the material to be mixed, to take precautions to prevent injury when the shaft is raised. These precautions comprise means for switching off the drive when the shaft is raised and a basket that is fixed around the shaft and extends as far as the mixer blades.

OBJECT OF THE INVENTION

The object of the invention is to provide, in a work-bench for machining dental models, a simple form of bearing member for the workpiece and safety device, together with easy changing of the milling cutter and simple dust removal.

SUMMARY OF THE INVENTION

This object is achieved by the features set forth in the claims.

The invention has the advantage that it provides a single part that serves both as an auxiliary bearing member for the workpiece and to prevent accidental contact with the cutter, while simplifying dust-removal and making quicker tool-changing possible.

BRIEF DESCRIPTION OF THE DRAWINGS

An embodiment of the invention will now be described by way of example with reference to the accompanying drawings, in which.

DETAILED DESCRIPTION OF A PREFERRED EMBODIMENT OF THE INVENTION

Figure 1:
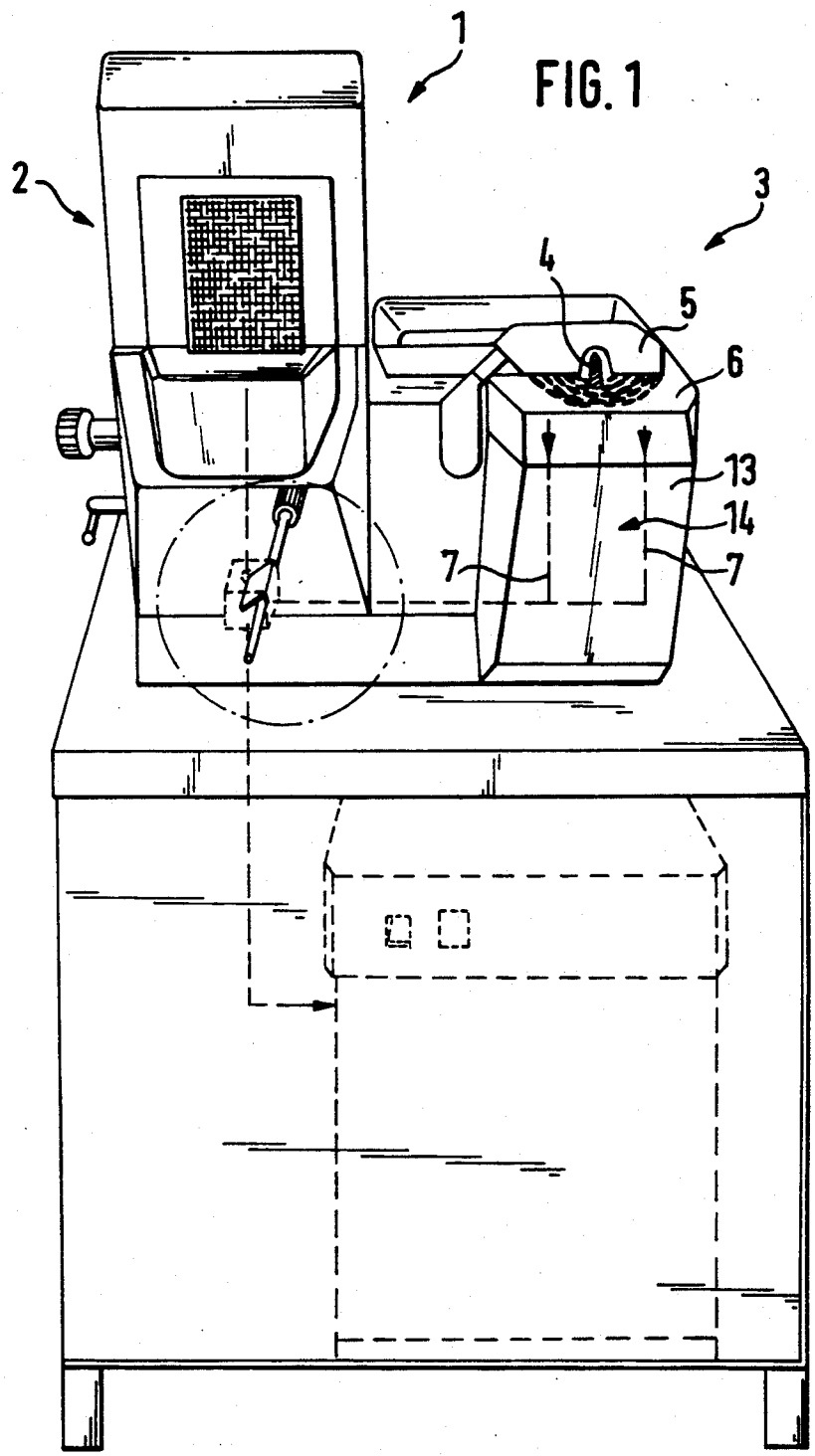
FIG. 1 is a general view of a machining bench in which the invention can be put into effect.

In FIG. 1, 1 is a combined machining bench comprising a belt grinder 2 and a milling machine 3.

FIG. 1 also shows the milling cutter 4 with a vertical axis, the auxiliary safety device 5 in the form of a pivoted lever forming the bearing member for the dental element to be machined, the milling table 6 and the exhaust passage 7.

These parts are arranged on a housing 13 that contains a driving motor 14 for the milling cutter 4.

Figure 2:
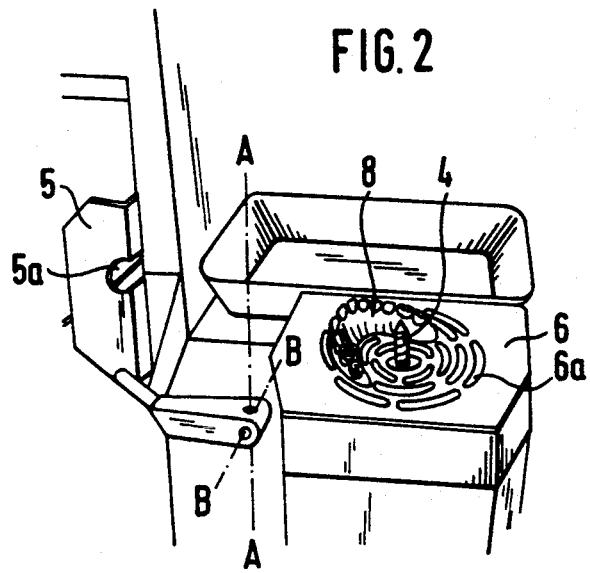
FIG. 2 is a detail of FIG. 1 showing the cutter and the auxiliary safety device in the opened position.

As shown in FIG. 2, the lever 5 can be pivoted about a vertical axis A—A and a horizontal axis B—B. These axes lie outside the milling machine 3. A recess 5a is formed in the lever so that the cutter 4 is covered when the lever 5 is swung down. Holes 6a are provided for the passage of dust that is formed.

Figure 3:
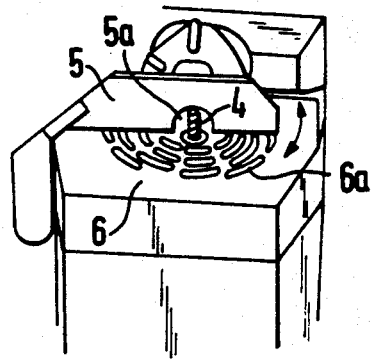
FIG. 3 is a detail of FIG. 2 with the auxiliary safety device in the closed position.

Arrows in FIG. 3 show how the lever 5 can be pivoted about the vertical axis A—A so that the workpiece 8 can be moved relative to the cutter 4 to determine the depth of the notch.

Figure 4:
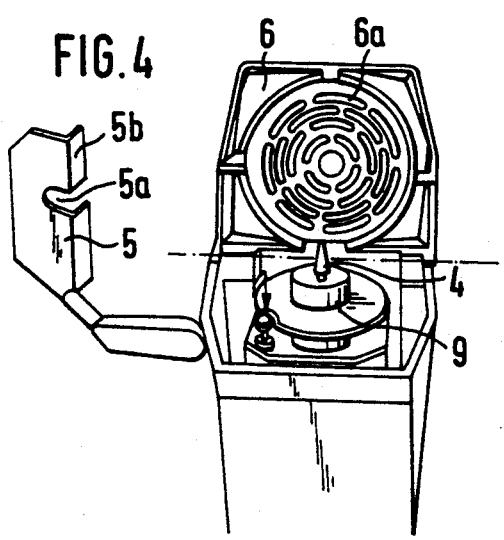
FIG. 4 is a view of the machining bench with the milling table in the opened position.

FIG. 4 shows how the milling table 6 can be swung up so that the cutter 4 can be simply changed. A centrifuge disc 9 can also be seen that is connected to the cutter 4 so as to rotate with it. It serves to protect the motor bearing from dust, which is flung away outwards to be sucked off through the exhaust passages 7.

Figure 5:
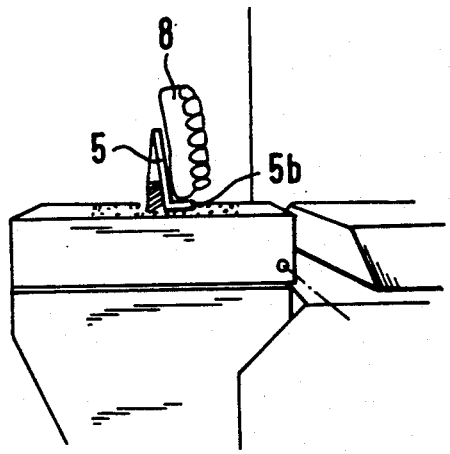
FIG. 5 is a side view with a workpiece is position.

FIG. 5 shows how the workpiece (the dental element 8) is placed on the lower flange of the L-shape of the lever 5, so that the milling position is always visible.

Figure 6:
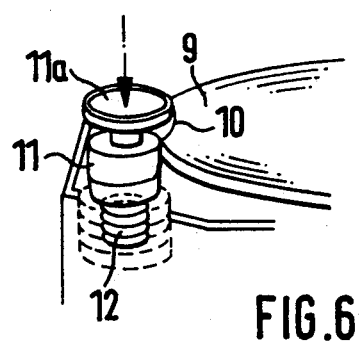
FIG. 6 shows means for arresting a centrifuge disc.

FIG. 6 shows an arresting device comprising a bolt 11 with a bolt head 11a. Under the pressure of a spring 12 the bolt is normally so positioned that the centrifuge disc 9 can rotate freely in an annular groove in the bolt 11. To change the cutter the bolt 11 is pressed down far enough for the bolt head 11a to engage in a recess 10 in the centrifuge disc, so that the disc can no longer rotate. In this position it is easy to change the cutter 4. To avoid having to hold the bolt 11 down by hand for an extended period of time securing means (not shown) to hold the bolt down in its depressed position for this time.

What is claimed is:

1. A work-bench for machining dental elements such as denture models and the like, comprising a housing, a driving motor located in said housing, a milling cutter driven by said motor and projecting upwardly from said housing, and a bearing member for said dental element to be machined that is arranged above said cutter and movable relative thereto, wherein said bearing member is mounted to be pivotable about a vertical axis above said milling cutter and pivotably mounted to be swung away from said milling cutter about a horizontal axis, said support being a pivotable and L-shaped lever in cross-section, said lever having a lower flange serving as the bearing member for said workpiece.

2. A work-bench for machining dental elements such as denture models and the like, comprising a housing, a driving motor located in said housing, a milling cutter driven by said motor and projecting upwardly from said housing, and a bearing member for said dental element to be machined that is arranged above said cutter and movable relative thereto, said bearing member being mounted to be pivotable about a vertical axis above said milling cutter and mounted to be swung away from said milling cutter about a horizontal axis; and including a milling table pivotably mounted so as to be swung upwardly and over said cutter.

3. A machining bench according to claim 1, wherein said lever is pivotable into a swung-in position covering said cutter.

4. A work-bench for machining dental elements such as denture models or the like, comprising a driving motor, a milling cutter driven by said driving motor and projecting upwardly from a housing containing said driving motor; and a bearing member for said dental elements to be machined arranged above said milling cutter and mounted so as to be movable relative thereto, said bearing member being mounted for pivoting about a vertical axis above said milling cutter and swingable away from said milling cutter about a horizontal axis, said bearing member being a lever having the horizontal pivoting axis thereof located below said milling cutter and externally of said housing.

5. A machining bench according to claim 3, wherein said lever is formed with a recess that covers said cutter when said lever is in its swung-in position.

6. A machining bench according to claim 1 which includes a milling table mounted so as to be swung upwardly.

7. A machining bench according to claim 6 wherein a centrifuge disc connected to said cutter is arranged below said milling table.

8. A machining bench according to claim 7, wherein said centrifuge disc has a recess in its periphery.

9. A machining bench according to claim 8 that includes an arresting device adapted to engage in said peripheral recess.

10. A machining bench according to claim 9, wherein said arresting device comprises a bolt the head of which can engage in said peripheral recess to effect arresting.

11. A machining bench according to claim 10, wherein said bolt is spring-loaded in the direction of freeing said centrifuge disc.

12. A machining bench according to claim 9 that includes means for securing said arresting device in its arresting position.

* * * * *